US008329880B2

(12) United States Patent
Jover et al.

(10) Patent No.: US 8,329,880 B2
(45) Date of Patent: Dec. 11, 2012

(54) PROCESS FOR THE PREPARATION OF NAPHTHALEN-2-YL-PYRAZOL-3-ONE INTERMEDIATES USEFUL IN THE SYNTHESIS OF SIGMA RECEPTOR INHIBITORS

(75) Inventors: Antoni Torrens Jover, Barcelona (ES); Jordi Corbera Arjona, Barcelona (ES); Maria Rosa Cuberes-Altisent, Barcelona (ES)

(73) Assignee: Laboratorios del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 12/988,922

(22) PCT Filed: Apr. 24, 2009

(86) PCT No.: PCT/EP2009/054981
§ 371 (c)(1),
(2), (4) Date: Dec. 1, 2010

(87) PCT Pub. No.: WO2009/130314
PCT Pub. Date: Oct. 29, 2009

(65) Prior Publication Data
US 2011/0071282 A1    Mar. 24, 2011

(30) Foreign Application Priority Data
Apr. 25, 2008   (EP) ................... 08384006

(51) Int. Cl.
C07D 231/22    (2006.01)
C07C 245/02    (2006.01)

(52) U.S. Cl. ........ 534/778; 534/565; 534/582; 534/590; 544/140; 546/211; 548/364.1; 548/369.4; 548/370.1; 548/371.1

(58) Field of Classification Search .............. None
See application file for complete search history.

(56) References Cited

U.S. PATENT DOCUMENTS

| | | | | |
|---|---|---|---|---|
| 2,908,677 A | * | 10/1959 | Straley et al. ............... | 534/710 |
| 3,514,439 A | * | 5/1970 | Wehrli et al. ............... | 534/711 |
| 3,980,675 A | * | 9/1976 | Venturello et al. ........... | 549/479 |
| 4,207,392 A | * | 6/1980 | Shiao et al. ................. | 430/352 |
| 4,234,479 A | * | 11/1980 | Mennicke et al. ............ | 534/698 |
| 4,234,616 A | | 11/1980 | Shu et al. | |
| 7,091,257 B2 | * | 8/2006 | Greer, IV ..................... | 522/96 |
| 7,105,646 B2 | * | 9/2006 | Chamberlain et al. ........ | 534/758 |
| 7,696,199 B2 | * | 4/2010 | Laggner et al. ............. | 514/227.8 |

FOREIGN PATENT DOCUMENTS

| | | | |
|---|---|---|---|
| GB | 1496411 | * | 12/1977 |
| GB | 2026482 A | | 7/1978 |
| JP | 10036259 | | 2/1998 |
| WO | 2006021462 A1 | | 3/2006 |
| WO | 2007098953 A1 | | 9/2007 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227.*
Vippagunta et al., Advanced Drug Delivery Reviews, 48, 3-26, 2001.*
Venturello, Carlo et al., "A Novel Synthesis of Pyrazol-3-ones Form Biacetyl Dimer and Arenediazonium Salts", Journal of the Chemical Society, Perkin Transactions I: Organic and Bio-organic Chemistry, (1972-1999), 7, 681-685, 1978.*
Ventuerello C., "2-Arylazo-2, 5-dimethyl-3-oxo-2, 3-dihydrofurans, useful intermediates in the synthesis of 1-aryl-5-methyl-3-pyrazolones", Synthesis, 1979, pp. 283-287.

(Continued)

*Primary Examiner* — Fiona T Powers
(74) *Attorney, Agent, or Firm* — Hoffmann & Baron, LLP

(57) ABSTRACT

The invention relates to a process for preparing naphthalen-2-yl-pyrazol-3-one intermediates, tautomers, and salts thereof, to novel intermediates, and to the use of the intermediates in the preparation of sigma receptor inhibitors.

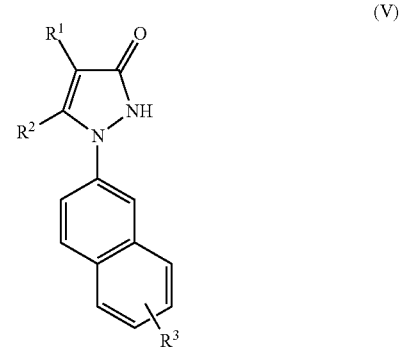

(V)

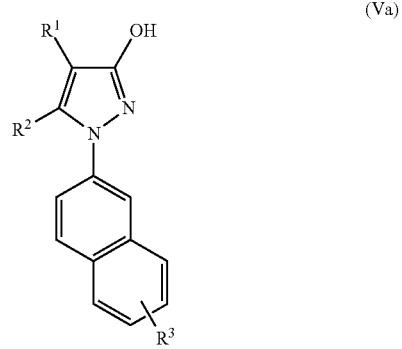

(Va)

11 Claims, No Drawings

OTHER PUBLICATIONS

Almerico AM., "1-Methyl-3H-pyrazolo[1, 2-a]benzo[1, 2, 3, 4] tetrazin-3-ones: Design, synthesis and biological activity of new antitumor agents", Journal of Medicinal Chemistry, vol. 48, 2005, pp. 2859-2866.
International Search Report for PCT/EP2009/054981, dated Jul. 24, 2009.
Walker et al., "Sigma Receptors: Biology and Function", Pharmacological Reviews, 42, pp. 355-402, 1990.
Effenberger et al., "Synthesen mit β-Äthoxy-acrylsäurechloriden" Chem. Ber., 102(10), pp. 3260-3267, 1969.
Eghbaldar et al., "Substances aromatisantes séparation chirale par chromatographie gazeuse" Parfums, Cosmetiques, Aromes, 104, pp. 71-78, 1992.
Mosandi et al., "Stereoisomeric Flavor Compounds XLIV: Enantioselective Analysis of Some Important Flavor Molecules", J. High Resol. Chromatog., 13(9), pp. 660-662, 1990.
Baraldi et al., "Ethyl 2,4-Dioxoalkanoates as Starting Materials for a Convenient Route to 3(2H)Furanones and 3(2H) Furanimines", Tetrahedron, vol. 43, No. 1, pp. 235-242, 1987.
Baraldi et al., "Ethyl 5-Substituted-3-Isoxazolecarboxylates as Starting Materials for a Convenient Route to 3(2H) Furanones and 3(2H)Iminofuranes", Tetrahedron Lett., 25(38), pp. 4313-4316; 1984.
Winkler et al., "Synthesis of Highly Functionalized Furanones via Aldol Reaction of 3-Silyloxyfurans", Organic Letters, vol. 7, No. 3, pp. 387-389, 2005.
Li et al., "Asymmetric Total Synthesis and Formal Total Synthesis of the Antitumor Sesquiterpenoid (+)-Eremantholide A", Organic Letters, vol. 9, No. 7, pp. 1267-1270, 2007.

Shu et al., "Parameter Effects on the Thermal Reaction of Cystine and 2,5-Dimethyl-4-hydroxy-3(2H)-furanone", ACS Symposium Letters, 409, pp. 229-241, 1989.
Batson et al., "α-Hydroxy Cyclopentenones from α-Diketones", Organic Letters, vol. 7, No. 13, pp. 2771-2774, 2005.
Coxon et al., "Acid-catalysed Rearrangements of trans- and cis-1-Acetoxy-3,4-epoxypentane and 1-Acetoxy-4,5-epoxyhexane", J. Chem. Soc. Chem. Commun., 8, pp. 261-262, 1973.
Yeretzian et al., "Analysing the headspace of coffee by proton-transfer-reaction mass-spectrometry", Int. J. Mass Spect., 223-224 (1-3), pp. 115-139, 2003.
Mukerji et al., "Addition of Nitrile Oxides to Olefins, Synthesis of Dihydrojasmone and Starting Material for Prostanoids. A Novel Route to Pyrroles", Tetrahedron, 39 (13) pp. 2231-2235, 1983.
Goodman and Gilman, "The Pharmacological Basis of Therapeutics", 8th Ed.; 13-18., 1992.
Horner et al., "Azo-aryle und Phenazine aus primären Arylaminanionen durch Autoxydation", Chem. Ber., 96, pp. 786-793, 1963.
LaBudde et al., "The Synthesis of the Mono- and Dihydroxy Derivatives of 1,2,5,6-Dibenzanthracene Excreted by the Rabbit and of Other Hydroxylated Dibenzanthracene Derivatives", J. Am. Chem. Soc., 80, pp. 1225-1236, 1958.
Renli et al., "Synthesis and Structure-Antitumor Activity of 4,6-Diamino-1,2-Dihydro-2,2-Dimethyl-1-(Substituted Naphthyl-2)-1,3,5-Triazines", Chem. Res. Chinese Univ., 7(3), pp. 197-200, 1991.
Mueller et al., "Some Derivatives of 7-Methoxy- and 10-Methoxybenzo (f) quinoline", J. Am. Chem. Soc., 66, pp. 860-862, 1944.

* cited by examiner

PROCESS FOR THE PREPARATION OF NAPHTHALEN-2-YL-PYRAZOL-3-ONE INTERMEDIATES USEFUL IN THE SYNTHESIS OF SIGMA RECEPTOR INHIBITORS

CROSS-REFERENCE TO RELATED APPLICATIONS

This application is the National Stage of International Application No. PCT/EP2009/054981, filed Apr. 24, 2009, which claims the benefit of European Application No. EP08384006.6, filed Apr. 25, 2008, the contents of which are incorporated by reference herein.

FIELD OF THE INVENTION

The invention relates to a process for preparing naphthalen-2-yl-pyrazol-3-one intermediates, tautomers, and salts thereof, to novel intermediates, and to the use of the intermediates in the preparation of sigma receptor inhibitors.

BACKGROUND OF THE INVENTION

Psychiatric and neurologic disorders are among the most severe and chronic diseases and conditions. These disorders are also extremely difficult to treat effectively because of the multiplicity of the symptoms and etiologies.

Amongst the therapeutic arsenal to combat these psychiatric and neurologic disorders, sigma receptor inhibitors have been found useful in the treatment of psychosis and movement disorders such as dystonia and tardive dyskinesia, and motor disturbances associated with Huntington's chorea or Tourette's syndrome and in Parkinson's disease (Walker, J. M. et al, *Pharmacological Reviews*, 1990, 42, 355).

WO2006021462 and WO2007098953 describe pyrazole-containing compounds having pharmacological activity towards the sigma receptor, being particularly useful in the therapy of pain, in particular neuropathic pain or allodynia. These compounds have the following chemical structure:

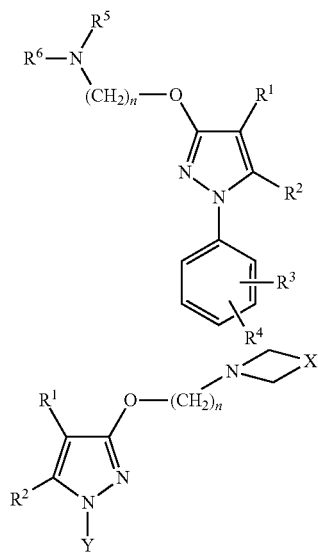

These compounds may be prepared according to the route schemes disclosed in WO2006021462 and WO2007098953.

Of particular interest are the intermediates represented by the formula (II) in said patent applications:

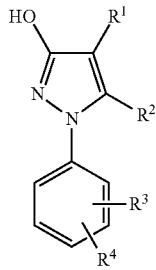

wherein $R^3$ and $R^4$, together with the phenyl ring to which they are attached form a naphthyl ring.

According to the routes presented in the mentioned patent applications, these intermediates can be prepared by reacting a acetohydrazide derivative with an ethyl acetoacetate; by reacting an hydrazine derivative with an ethyl butynoate; or by the method provided by F. Effenberger and W. Hartmann, *Chem. Ber.*, 102(10), 3260-3267, 1969, where an ethoxyacrylic acid hydrazide is reacted with concentrated mineral acid.

C. Venturello and R. D'Aloisio, *Synthesis* 1979, describes a process to synthesize 2-arylazo-2,5-dimethyl-3-oxo-2,3-dihydrofurans, which are useful intermediates in the synthesis of 1-aryl-5-methyl-3-pyrazolones. In said process, 1-aryl-5-methyl-3-oxo-2,3-dihydropyrazoles (5) are prepared according to method A by adding to concentrated hydrochloric acid while is taken care that the temperature of the mixture does not exceed 30° C. In Method B, 2-arylazo-2,5-dimethyl-3-oxo-2,3-dihydrofuran (3) is dissolved in an acetic/concentrated hydrochloric acid mixture (12.5:1 v/v; 10 ml), keeping the solution at 25-50° C.

In the methods provided by Venturello et al., the exemplified aryl derivatives are all restricted to phenyl-containing compounds. Phenyl and naphthyl rings have distinct reactivity due to a difference in the n-stabilization energy of the aromatic rings. In addition, the naphthyl radical introduces a bigger steric hindrance that the phenyl radical. Moreover, these methods are devised for a laboratory environment, and have not been validated for a scalable process.

During pharmaceutical development, optimized processes to synthesize molecules such as intermediates or final products are sought. Increased yields, purity, simplification of the routes, and the provision of up-scalable processes are amongst the objectives for the chemical developers. Often, chemists are challenged with finding that specific balance between an up-scalable process and a sufficient purity or yield. The use of not too extreme conditions during the process, as well as the use of non-toxic reagents, is part of the equation that the chemist needs to solve.

Hence, an objective of the present invention is to provide a process for the preparation of naphthalen-2-yl-pyrazol-3-one intermediates, which process can improve at least one or more of the following process related parameters, i.e. purity, yield, simplification of the synthetic route, use of affordable conditions, use of environmental-friendly conditions, use of non-toxic reagents, or improved processability of the reagents or final intermediate products.

SUMMARY OF THE INVENTION

The present invention concerns a process for preparing an intermediate in the synthesis of pyrazole-containing compounds useful in the therapy of pain, in particular it concerns a process for preparing a compound of formula (V), a tautomer (Va), and salts thereof,

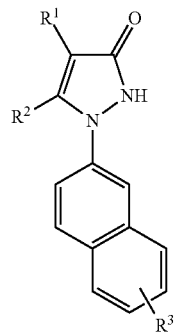
(V)

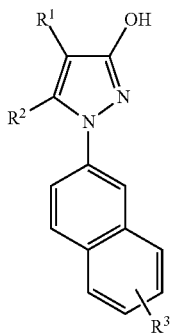
(Va)

wherein a compound of formula (IV) is submitted to acidic conditions at a temperature between 15 and 80° C.,

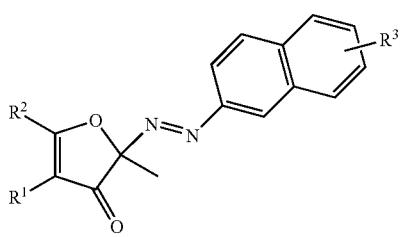
(IV)

thereby obtaining a compound of formula (V), a tautomer (Va), or a salt thereof;
wherein in compounds of formula (V), (Va), and (IV),
$R^1$ is hydrogen, $C_{1-6}$alkyl, or —C(=O)$R^4$;
$R^2$ is hydrogen, $C_{1-6}$alkyl, or phenyl;
$R^3$ is hydrogen or $C_{1-6}$alkoxy; and
$R^4$ is hydrogen or $C_{1-4}$alkyl.

In a further embodiment, the present invention provides the compounds of formula (V), (Va), (IV), per se, wherein $R^1$, $R^2$, and $R^3$ are as defined above.

In a further embodiment, the invention refers to the use of the compounds of formula (V), (Va), and (IV) as intermediates in the preparation of a compound of formula (X), pharmaceutically acceptable salts, isomers, prodrugs, and solvates thereof.

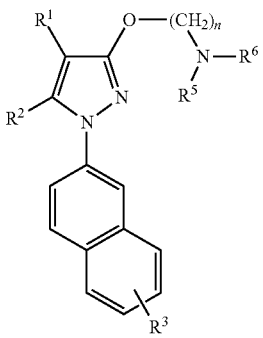
(X)

DISCLOSURE OF THE INVENTION

In an attempt to optimize for large scale production the synthetic routes leading to the naphthalen-2-yl-pyrazol-3-ones intermediates, the inventors have envisaged a method and have surprisingly found that said method not only works and results in an increased yield versus the prior art methods, but that it allows the industrial production of these intermediates with, importantly, a high degree of purity.

The present invention relates to a method for the preparation of a compound of formula (V), a tautomer (Va), and salts thereof,

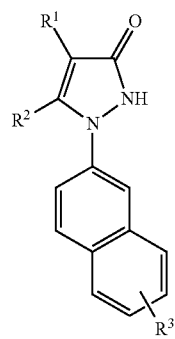
(V)

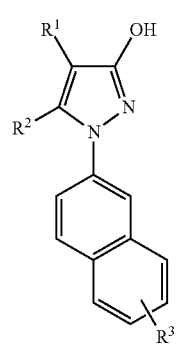
(Va)

said method comprising submitting a compound of formula (IV) to acidic conditions at a temperature between 15 and 80° C.,

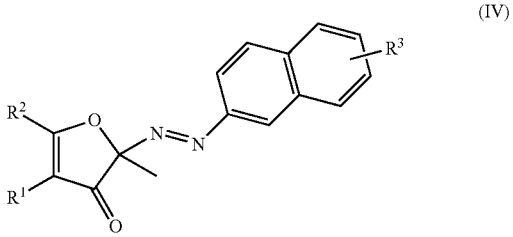

(IV)

thereby obtaining a compound of formula (V), a tautomer (Va), or a salt thereof;
wherein in compounds of formula (V), (Va), and (IV),
$R^1$ is hydrogen, $C_{1-6}$alkyl, or —C(=O)$R^4$;
$R^2$ is hydrogen, $C_{1-6}$alkyl, or phenyl;
$R^3$ is hydrogen or $C_{1-6}$alkoxy; and
$R^4$ is hydrogen or $C_{1-4}$alkyl.

As used hereinbefore or hereinafter $C_{1-4}$alkyl as a group or part of a group defines straight or branched chain saturated hydrocarbon radicals having from 1 to 4 carbon atoms such as methyl, ethyl, propyl, 1-methylethyl, butyl; $C_{1-6}$alkyl as a group or part of a group defines straight or branched chain saturated hydrocarbon radicals having from 1 to 6 carbon atoms such as the group defined for $C_{1-4}$alkyl and pentyl, hexyl, 2-methylbutyl, and the like.

The term $C_{1-6}$alkoxy means $C_{1-6}$alkyloxy or a $C_{1-6}$alkyl ether radical, wherein the term $C_{1-6}$alkyl is as defined above. Examples of suitable alkyl ether radicals include methoxy, ethoxy, n-propoxy, isopropoxy, n-butoxy, iso-butoxy, sec-butoxy, tert-butoxy, hexanoxy and the like.

The term halide is generic to fluorine, chlorine, bromine, and iodine.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

In one embodiment of the present invention, in those compounds of formulae (V), (Va), (IV), (II), and (I), the naphthyl ring may be substituted by $R^3$ in each of the positions 1, 3, 4, 5, 6, 7, and 8. In a preferred embodiment, the naphthyl ring is unsubstituted, i.e. $R^3$ is hydrogen. In another embodiment, the naphthyl ring is substituted in positions 5, 6, or 7 by a $C_{1-6}$alkoxy group, preferably selected from methoxy, ethoxy, n-propoxy, and isopropoxy.

In another embodiment of the present invention, in those compounds represented by formulae (V), (Va), (IV), and (III), $R^1$ is selected from hydrogen, methyl, ethyl, propyl, isopropyl, and —C(=O)$R^4$, wherein $R^4$ is hydrogen, methyl, or ethyl. Preferably, $R^1$ is selected from hydrogen, methyl, and —C(=O)$R^4$, wherein $R^4$ is methyl. More preferably $R^1$ is hydrogen.

In a further embodiment of the present invention, in those compounds represented by formulae (V), (Va), (IV), and (III), $R^2$ is selected from hydrogen, methyl, ethyl, propyl, isopropyl, and phenyl. Preferably, $R^2$ is selected from hydrogen, methyl, isopropyl, and phenyl. More preferably $R^2$ is methyl.

The term "salt" as mentioned herein is meant to comprise any stable salts, which the intermediates of formula (V) or (Va) are able to form. Preferred are the pharmaceutically acceptable salts, which are the non-toxic salt forms. Salts that are not pharmaceutically acceptable are also embraced in the scope of the present invention, since they refer to intermediates that are useful in the preparation of compounds with pharmacological activity. The salts can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propane-tricarboxylic, methanesulfonic, ethanesulfonic, benzenesulfonic, 4-methylbenzene-sulfonic, cyclohexanesulfamic, 2-hydroxybenzoic, 4-amino-2-hydroxybenzoic and similar acids. Conversely, the salt form can be converted by treatment with alkali into the free base form. The term "salts" is also meant to include the hydrates or solvates which the compounds of formula (V) and (Va) are able to form, including, e.g. alcoholates, such as methanolates or ethanolates.

The phrase "pharmaceutically acceptable" refers to molecular entities and compositions that do not produce adverse, allergic, or other untoward reactions when administered to an animal or a human.

Compounds of formula (IV) are submitted to acidic conditions at a temperature between 15 and 80° C. to obtain compounds of formula (V), (Va), or salts thereof.

The term "acidic conditions" refers to acids such as hydrochloric acid, acetic acid, trifluoroacetic acid, formic acid, sulphonic acid, sulfuric acid, phosphoric acid, mixtures thereof, and the like. These acids may be employed in diluted or concentrated form, such as concentrated hydrochloric. The hydrochloric acid is used at approximately a concentration 1N-12N, preferably, at 3N to 9N, more preferably, at 5N to 7N, and even more preferably, at about 6N. Preferably, "acidic conditions" refers to a pH<3 solution setting.

In one embodiment, a mixture of acetic acid and hydrochloric acid is employed, preferably, in a ratio of 1 to 5 volumes of acetic acid to 1 volume of hydrochloric acid, and more preferably, in a ratio of 2 to 3 volumes of acetic acid to 1 volume of hydrochloric acid.

The temperature of the reaction ranges from 15 to 80° C. Preferred reaction temperatures are selected in the range of 20 to 75° C., more preferably, in the range of 30 to 70° C., and even more preferably, in the range of 45 to 65° C.

It is evident that in the foregoing and in the following reactions, the reaction products may be isolated from the reaction medium and, if necessary, further purified according to methodologies generally known in the art such as extraction, crystallization and chromatography.

In one embodiment of the present invention, the compound of formula (IV) is prepared by reacting a compound of formula (II) with a compound of formula (III) in an aqueous medium at a pH below 1,

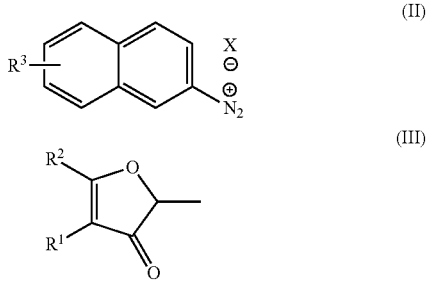

wherein in compounds of formula (II) and (III),
X is halide, nitrate, phosphate, sulfate, borate, or tetrafluoroborate; and
$R^1$, $R^2$, and $R^3$ are as defined above.

Starting materials of formula (III) of the present invention are available commercially or from known methods in the art as disclosed in the following list:

2,5-dimethyl-3(2H)-furanone, from Ryan Scientific Product List.

4-(1,1-dimethylethyl)-2,5-dimethyl-3(2H)-furanone, from JP10036259.

(S)-2,5-dimethyl-3(2H)-furanone and (R)-2,5-dimethyl-(2H)-furanone, from Eghbaldar et al., Parfums, Cosmetiques, Aromes (1992), 104, 71-8.

(R)-5-hexyl-2-methyl-3(2H)-furanone and (S)-5-hexyl-2-methyl-3(2H)-furanone, from Mosandl et al. Journal of High Resolution Chromatography (1990), 13(9), 660-2.

2-methyl-4-(2-methylpropyl)-3(2H)-furanone and 2-methyl-4-pentyl-3(2H)-furanone, from Baraldi et al. Tetrahedron (1987), 43(1), 235-42.

2-methyl-5-(2-methylpropyl)-3(2H)-furanone, 2-methyl-5-phenyl-3(2H)-furanone, and 2-methyl-5-pentyl-3(2H)-furanone, from Baraldi et al. Tetrahedron Letters (1984), 25(38), 4313-16.

5-hexyl-2-methyl-3(2H)-furanone, from Winkler et al. Organic Letters (2005), 7(3), 387-389.

5-ethyl-2-methyl-3(2H)-furanone, from Li et al. Organic Letters (2007), 9(7), 1267-1270.

5-ethyl-2,4-dimethyl-3(2H)-furanone, from Shu et al. ACS Symposium Series (1989), Volume Date 1988, 409(Therm. Gener. Aromas), 229-41.

2,4-dimethyl-5-phenyl-3(2H)-furanone, from Batson et al. Organic Letters (2005), 7(13), 2771-2774.

2,4,5-trimethyl-3(2H)-furanone, from U.S. Pat. No. 4,234,616 or GB2026482.

2-methyl-3(2H)-furanone, from Coxon et al. Journal of the Chemical Society, Chemical Communications (1973), (8), 261-2.

2,4-dimethyl-3(2H)-furanone, from Yeretzian et al. International Journal of Mass Spectrometry (2003), 223-224(1-3), 115-139.

5-isopropyl-2-methyl-3(2H)-furanone, from Mukerji et al, Tetrahedron (1983), 39(13), 2231-5.

The aqueous medium referred herein also includes water.

To obtain a pH below 1 at the reaction mixture comprising a compounds of formula (II) and (III) in an aqueous medium, concentrated acids such as hydrochloric acid, hydrofluoric acid, nitric acid, phosphoric acid, sulfuric acid, boric acid, and tetrafluoroboric acid may be added. Preferably, concentrated hydrochloric acid is used.

An advantage of the processes presented herein is that after reacting compounds of formula (II) and (III), it is not necessary to purify the resulting compound of formula (IV). The organic phase comprising a compound of formula (IV) can be readily submitted to the acidic conditions at a temperature between 15 and 80° C. as described above, thereby obtaining a compound of formula (V), a tautomer (Va), or a salt thereof.

As such, one embodiment of the present invention refers to a method for the preparation of a compound of formula (V), a tautomer (Va), and salts thereof, said method comprising reacting a compound of formula (II) with a compound of formula (III) in an aqueous medium at a pH below 1, thereby obtaining a reaction mixture comprising a compound of formula (IV). The organic phase thereof is then submitted to acidic conditions at a temperature between 15 and 80° C., thereby obtaining a compound of formula (V), a tautomer (Va), or a salt thereof; wherein X, $R^1$, $R^2$, and $R^3$ are as defined above in compounds of formula (II), (III), (IV), (V), and (Va).

Optionally, would a separation of compound of formula (IV) from the organic phase be desired, said compound may be separated by filtration of the aqueous phase. If compound of formula (IV) is not miscible in water, the compound can be separated by pouring or by liquid-liquid extraction.

Compounds of formula (III) and (IV) have at least one center of chirality (indicated below with an asterisk) and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (III) or (IV) may possess.

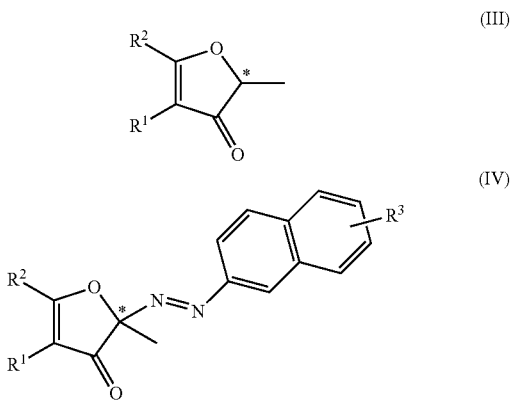

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compounds may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

In one embodiment of the present invention, the compound of formula (II) is prepared by reacting compound of formula (I) with a nitrous acid solution in an aqueous medium at a temperature between −10 and 10° C.,

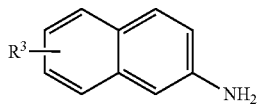

(I)

wherein,
$R^3$ is as defined above.

The nitrous acid solution may be prepared by reacting a mineral acid with sodium nitrite. Suitable mineral acids for preparing the nitrous acid solution include hydrochloric acid, hydrofluoric acid, nitric acid, phosphoric acid, sulfuric acid, boric acid, and tetrafluoroboric acid.

The reaction temperature employed in the preparation of compound of formula (II) is suitably selected between −10 and 10° C., preferably between −5 and 5° C., and more preferably at approximately 0° C.

Starting materials of formula (I) are commercially available or may be easily obtained from commercially available products, by known methods in the art. As an example, there can be mentioned:
5-methoxy-2-naphthalenamine, from Chemstep.
2-aminonaphthalene, from Sigma.
2-naphthalenamine, hydrobromide, from Salor.
2-naphthylamine hydrochloride, from International Laboratory.
6-methoxy-2-naphthalenamine, from Chemstep.
7-methoxy-2-naphthalenamine, from Chemstep.
8-methoxy-2-naphthylamine, from Horner, et al. Chemische Berichte (1963), 96, 786-97.
7-methoxy-2-naphthylamine hydrochloride, from LaBudde et al. Journal of the American Chemical Society (1958), 80, 1225-36.
6-propoxy-2-naphthalenamine, from Li et al. Chemical Research in Chinese Universities (1991), 7(3), 197-200.
8-methoxy-2-naphthylamine hydrochloride and 5-methoxy-2-naphthylamine hydrochloride, from Mueller et al. Journal of the American Chemical Society (1944), 66, 860-2.

In the above-mentioned respective reactions, each of the obtained compounds, when necessary, can be collected from the reaction mixture according to methods known in the art. For example, when insoluble materials are present, the desired compound can be obtained—after removing the insoluble materials by filtration—by removing the solvent, e.g. by removing the solvent under reduced pressure, and/or by adding water to the residue and extracting the mixture with a water-immiscible organic solvent such as ethyl acetate, etc. Optionally, the desired compound can be obtained after drying over anhydrous sodium sulfate, for instance, and further, if necessary, by purifying with any conventional method, such as recrystallization, column chromatography, or other techniques.

Another embodiment of the present invention refers to a compound of formula (V), a tautomer (Va), and salts thereof, per se

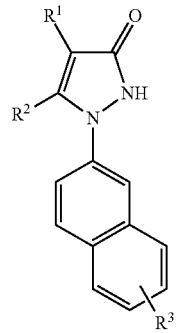

(V)

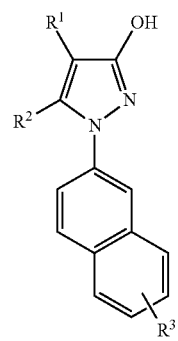

(Va)

wherein,
$R^1$ is hydrogen, $C_{1-6}$alkyl, or —C(=O)$R^4$;
$R^2$ is hydrogen, $C_{1-6}$alkyl, or phenyl;
$R^3$ is hydrogen or $C_{1-6}$alkoxy; and
$R^4$ is hydrogen or $C_{1-4}$alkyl.

Examples of specific compounds of formula (V) or (Va) in accordance with the invention include compound Nos. 1, 2, 3, and 4, referred to in the Examples below, and the salts thereof.

Another embodiment of the present invention refers to a compound of formula (IV) per se,

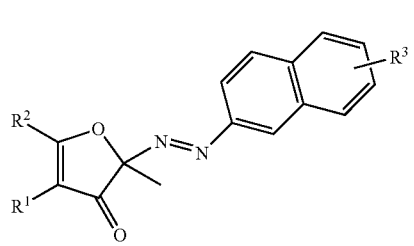

(IV)

wherein,
$R^1$ is hydrogen, $C_{1-6}$alkyl, or —C(=O)$R^4$;
$R^2$ is hydrogen, $C_{1-6}$alkyl, or phenyl;
$R^3$ is hydrogen or $C_{1-6}$alkoxy; and
$R^4$ is hydrogen or $C_{1-4}$alkyl.

The different compounds encompassed by formulae (V) or (Va) may be converted into each other following art-known functional group transformation reactions. Suitably, they are obtained with starting materials, i.e. compounds of formula (I) and (III) already embracing the desired substituents $R^1$, $R^2$, or $R^3$.

The compounds of formula (V) or (Va) of the present invention may be converted to the corresponding N-oxide forms following art-known procedures for converting a trivalent nitrogen into its N-oxide form. The N-oxide forms of the present compounds are meant to comprise the compounds of formula (V) or (Va) wherein one or several nitrogen atoms are oxidized to the so-called N-oxide. Said N-oxidation reaction may generally be carried out by reacting compound of formula (V) or (Va) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Due to their favorable processability properties, as will be apparent from the examples, the compounds of the present invention are useful as intermediates in the preparation of a compound of formula (X) as defined above. In general, the compounds of the present invention are useful in the preparation of a compound of formula (X), pharmaceutically acceptable salts, isomers, prodrugs, and solvates thereof, which has pharmacological activity against the sigma receptor—a cell surface receptor of the central nervous system, which is said to be related to the dysphoric, hallucinogenic and cardiac stimulant effects of opioids.

As such, one embodiment of the present invention refers to the use of compounds of formula (V), a tautomer (Va), and salts thereof as intermediates in the preparation of a compound of formula (X), pharmaceutically acceptable salts, isomers, prodrugs, and solvates thereof,

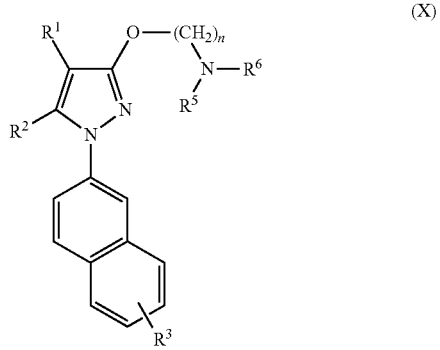

wherein,
$R^1$, $R^2$, and $R^3$ are as defined above;
n is 2; and
$R^5$ and $R^6$ are, each independently, $C_{1-6}$alkyl, or together with the nitrogen atom to which they are attached form a morpholinyl, piperidinyl, or pyrrolidinyl group.

Another embodiment of the present invention refers to the use of compounds of formula (IV), (III), (II), and (I), each independently, as intermediates in the preparation of a compound of formula (X), pharmaceutically acceptable salts, isomers, prodrugs, and solvates thereof, as referred to herein above.

The term "prodrug" as used throughout this text means the pharmacologically acceptable derivatives such as esters, amides and phosphates, such that the resulting in vivo biotransformation product of the derivative is the active drug as defined in the compounds of formula (X). The reference by Goodman and Gilman (The Pharmaco-logical Basis of Therapeutics, 8th ed, McGraw-1-Till, hit. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

The term "solvate" refers to those crystal forms of the compounds of formula (X) that contain either stoichiometric or non-stoichiometric amounts of solvent. Since water is a solvent, solvates also include hydrates.

The term "pseudopolymorph" is synonym to solvate since it applies to polymorphic crystalline forms that have solvent molecules incorporated in their lattice structures.

Examples of solvates are hydrates and alcoholates such as methanolates or ethanolates.

The following specific examples are provided to further illustrate the invention and various preferred embodiments.

EXAMPLES

Example 1

Synthesis of 2,5-dimethyl-2-(naphthalen-2-yldiazenyl)furan-3(2H)-one

To a suspension of naphthalen-2-amine (2.86 g, 20 mmol) in $H_2O$ (12 mL) was added HCl conc. (5 mL) and cooled in an ice bath, and subsequently, a $NaNO_2$ solution (1.48 g, 21.5 mmol in $H_2O$ (8 mL)) was added drop-wise maintaining the stirring mixture at 0° C. during 20 minutes.

The previous solution was diluted in $H_2O$ (25 mL) and 2,5-dimethylfuran-3(2H)-one (2.48 g, 22 mmol) was added, and left stirring during 1.5 hours at a room temperature, thereby resulting in a thick oil of orange color. Ethyl ether was added and the organic phase was washed with water, saturated solution of $NaHCO_3$ and water. The organic phase was poured, dried, and eliminated at a reduced pressure thereby obtaining 2,5-dimethyl-2-(naphthalen-2-yldiazenyl)furan-3(2H)-one (4.5 g, 16.9 mmol, 84.5%) in the form of a thick oil of orange color that solidified on standing and that could be used in the following reaction without purification.

In fact, the previously mentioned crude oil was purified, prior to the next synthetic step by chromatography on silica gel using $CH_2Cl_2$ as eluant obtaining 2,5-dimethyl-2-(naphthalen-2-yldiazenyl)furan-3(2H)-one (3.4 g, 12.8 mmol, 64.0%) as an orange solid material. M.p. 76-77° C.

$^1$H NMR (300 MHz, $CDCl_3$) δ 1.80 (s, 3H), 2.48 (s, 3H), 5.56 (5, 1H), 7.56 (m, 2H), 7.79-7.89 (m, 3H), 7.98 (m, 1H), 8.42 (s, 1H).

Example 2

Synthesis of 5-methyl-1-(naphthalen-2-yl)-1H-pyrazol-3(2H)-one (Compound 1)

2,5-dimethyl-2-(naphthalen-2-yldiazenyl)furan-3(2H)-one (2.0 g, 7.51 mmol) dissolved in acetic acid (15 mL) was added on a mixture of acetic acid (10 mL) and 6N hydrochloric acid (10 mL) previously heated to a temperature of 65° C. (58° C. interior temperature). The mixture was kept on stirring and at the same temperature of 65° C. for a period of 2 hours. The solution was cooled, a mixture of water/ice (200 mL) was added and the resulting solid material was filtered and washed with water. The resulting crude (1.27 g, purity HPLC 94%) was suspended in water (40-50 mL), NaOH 10% was added until achieving a basic pH (10-12), the insoluble impurities were filtered, the solution was acidified with HCl 2N and the obtained precipitate was filtered and washed with water thereby obtaining 5-methyl-1-(naphthalen-2-yl)-1H-pyrazol-3(2H)-one (1.09 g, 4.86 mmol, 65%, purity HPLC 96% without re-crystallization).

$^1$H NMR (300 MHz, DMSO-$d_6$) δ 2.36 (s, 3H), 5.64 (s, 1H), 7.54 (m, 2H), 7.69 (m, 1H), 7.93-8.02 (m, 4H), 9.97 (s, 1H).

Example 3

Additional compounds that were prepared following the methods described in Examples 1 and 2 were:

| Compound nr. | Name | $^1$H-NMR δ ppm | MS |
|---|---|---|---|
| 2 | 1-(6-methoxynaphthalen-2-yl)-5-methyl-1H-pyrazol-3-ol | CDCl$_3$: 7.8 (d, J = 8.8 Hz, 1H), 7.75 (d, J = 8.9 Hz, 1H), 7.7 (d, J = 1.8 Hz, 1H), 7.5 (dd, J = 2.2 and 8.65 Hz, 1H), 7.2 (dd, J = 2.4 and 8.9 Hz, 1H), 7.15 (d, J = 2.3 Hz, 1H), 5.6 (s, 1H), 3.95 (s, 3H), 2.3 (s, 3H). | 254 |
| 3 | 1-(7-methoxynaphthalen-2-yl)-5-methyl-1H-pyrazol-3-ol | DMSO-$d_6$: δ.9.95 (s, 1H), 7.9 (d, J = 8.8 Hz, 1H), 7.85 (m, 2H), 7.45 (dd, J = 2.0 and 8.8 Hz, 1H), 7.35 (d, J = 2.5 Hz, 1H), 7.15 (dd, J = 2.5 and 8.9 Hz, 1H), 5.6 (s, 1H), 3.85 (s, 3H), 2.35 (s, 3H). | 254 |
| 4 | 1-(5-methoxynaphthalen-2-yl)-5-methyl-1H-pyrazol-3(2H)-one beige solid m.p.: 206-8° C. | DMSO-$d_6$: δ.2.92 (s, 3H), 3.98 (s, 3H), 5.64 (s, 1H), 6.98 (d, J = 7.5 Hz, 1H), 7.49 (m, 2H), 7.64 (dd, J = 9.1 Hz, J' = 2.1 Hz, 1H), 7.91 (d, J = 2.1 Hz, 1H), 8.20 (d, J = 9.1 Hz, 1H), 9.86 (s, 1H). | — |

The invention claimed is:

1. A method for the preparation of a compound of formula (V), a tautomer (Va), or a salt thereof,

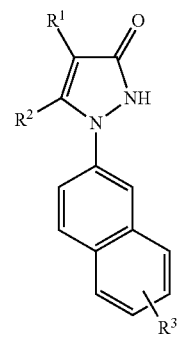

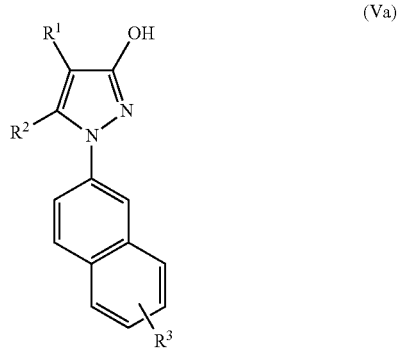

said method comprising submitting a compound of formula (IV) to acidic conditions at a temperature between 15 and 80 ° C.,

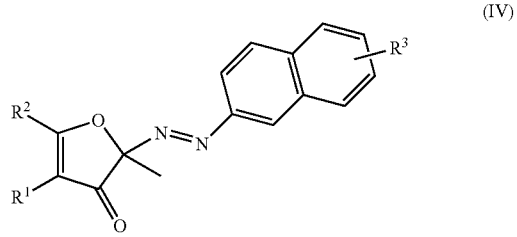

thereby obtaining a compound of formula (V), a tautomer (Va), or a salt thereof;

wherein in compounds of formula (V), (Va), and (IV), $R^1$ is hydrogen, $C_{1-6}$alkyl, or —C(=O)$R^4$;

$R^2$ is hydrogen, $C_{1-6}$alkyl, or phenyl;

$R^3$ is hydrogen or $C_{1-6}$alkoxy; and $R^4$ is hydrogen or $C_{1-4}$alkyl.

2. The method according to claim 1, wherein the acidic conditions comprise concentrated hydrochloric acid, or a mixture of acetic acid and concentrated hydrochloric acid.

3. The method according to claim 1, wherein the temperature is between 45 and 65 ° C.

4. The method according to claim 1, wherein the compound of formula (IV) is prepared by reacting a compound of formula (II) with a compound of formula (III) in an aqueous medium at a pH below 1, $$\text{(II)} \quad R^3 \text{—Naphthalene—} N_2^+ \; X^-$$

$$\text{(III)} \quad \text{(structure with } R^1, R^2, \text{methyl, O, C=O)}$$

wherein in compounds of formula (II) and (III),
X is selected from the group consisting of halide, nitrate, phosphate, sulfate, borate, and tetrafluoroborate; and
$R^1$, $R^2$, and $R^3$ are as defined in claim 1.

5. The method according to claim 4, wherein the compound of formula (II) is prepared by reacting compound of formula (I) with a nitrous acid solution in an aqueous medium at a temperature between −10 and 10 °C., $$\text{(I)} \quad R^3 \text{—Naphthalene—} NH_2$$

wherein $R^3$ is hydrogen or $C_{1-6}$alkoxy.

6. A compound of formula (IV), $$\text{(IV)}$$

wherein,
$R^1$ is hydrogen, $C_{1-6}$alkyl, or —C(=O)$R^4$;
$R^2$ is hydrogen, $C_{1-6}$alkyl, or phenyl;
$R^3$ is hydrogen or $C_{1-6}$alkoxy; and
$R^4$ is hydrogen or $C_{1-4}$alkyl.

7. A method for the preparation of a compound of formula (X), or a pharmaceutically acceptable salt, stereoisomer, or prodrug thereof $$\text{(X)}$$

wherein,
$R^1$ is hydrogen, $C_{1-6}$ alkyl, or —C(=O)$R^4$;
$R^2$ is hydrogen, $C_{1-6}$ alkyl, or phenyl;
$R^3$ is hydrogen or $C_{1-6}$ alkoxy;
$R^4$ is hydrogen or $C_{1-4}$ alkyl;
n is 2; and $R^5$ and $R^6$ are, each independently, $C_{1-6}$ alkyl, or together with the nitrogen atom to which they are attached form a morpholinyl, piperidinyl, or pyrrolidinyl group, which comprises the reaction of a compound of formula (V), a tautomer (Va), or a salt thereof, $$\text{(V)}$$

$$\text{(Va)}$$

with a compound of formula $$Cl\text{—}(CH_2)_n\text{—}N(R^5)\text{—}R^6.$$

8. A method for the preparation of a compound of formula (X), or a pharmaceutically acceptable salt, stereoisomer, or prodrug thereof, $$\text{(X)}$$

wherein, $R^1$ is hydrogen, $C_{1-6}$ alkyl, or —C(=O)$R^4$;

$R^2$ is hydrogen, $C_{1-6}$ alkyl, or phenyl;

$R^3$ is hydrogen or $C_{1-6}$ alkoxy;

$R^4$ is hydrogen or $C_{1-4}$ alkyl;

n is 2; and $R^5$ and $R^6$ are, each independently, $C_{1-6}$ alkyl, or together with the nitrogen atom to which they are attached form a morpholinyl, piperidinyl, or pyrrolidinyl group, which comprises:

a) submitting a compound of formula (IV) according to claim 6 to acidic conditions at a temperature between 15 and 80° C. to produce a compound of formula (V), a tautomer (Va), or a salt thereof

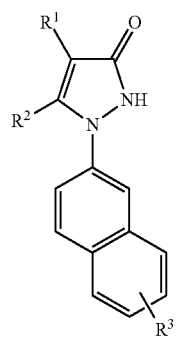
(V)

and

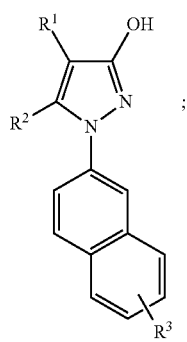
(Va)

b) reacting the compound of formula (V), a tautomer (Va), or a salt thereof with a compound of formula

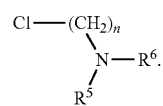

9. The compound according to claim 6, wherein $R^3$ is selected from hydrogen, methoxy, ethoxy, n-propoxy, and isopropoxy.

10. The compound according to claim 6, wherein $R^1$ is selected from hydrogen, methyl, ethyl, propyl, isopropyl, and —C(=O)$R^4$, wherein $R^4$ is hydrogen, methyl, or ethyl.

11. The compound according to claim 6, wherein $R^2$ is selected from hydrogen, methyl, ethyl, propyl, isopropyl, and phenyl.

* * * * *